United States Patent [19]

Hodgins et al.

[11] 4,229,537
[45] Oct. 21, 1980

[54] PREPARATION OF TRICHLORO-S-TRIAZINE ACTIVATED SUPPORTS FOR COUPLING LIGANDS

[75] Inventors: Leonard T. Hodgins, New York, N.Y.; Thomas H. Finlay, Ridgewood, N.J.; Alan J. Johnson, New York, N.Y.

[73] Assignee: New York University, New York, N.Y.

[21] Appl. No.: 876,240

[22] Filed: Feb. 9, 1978

[51] Int. Cl.$^2$ ............................ C07G 7/00; C07G 7/02
[52] U.S. Cl. ........................................ 435/177; 260/6; 435/178; 435/180; 435/181; 435/815; 544/217
[58] Field of Search ............... 195/63, 68, DIG. 11; 260/112 R, 6; 544/217; 435/174, 177, 178, 815, 179, 180, 181

[56] References Cited

U.S. PATENT DOCUMENTS

| 3,619,371 | 11/1971 | Crook et al. | 195/63 |
| 3,674,767 | 7/1972 | Lilly et al. | 195/63 X |
| 3,788,948 | 1/1974 | Kagedal et al. | 195/63 X |
| 3,824,150 | 7/1974 | Lilly et al. | 195/63 |
| 3,876,501 | 4/1975 | Hanushewsky | 195/63 X |
| 4,007,089 | 2/1977 | Smith | 195/63 X |
| 4,119,494 | 10/1978 | Durand et al. | 195/68 |

OTHER PUBLICATIONS

Kay et al., The Chemical Attachment of Chymotrypsin to Water-Insoluble Polymers Using 2-Amino-4,6-Dichloro-s-Triazine, Biochimicz et Biophysicz Acta, vol. 198, 1970 (pp. 276-285).

Abuchowski et al., Alteration of Immunological Properties of Bovine Serum Albumin by Covalent Attachment of Polyethylene Glycol, J. Biol. Chem., vol. 252, No. 11, 1977 (pp. 3578-3581).

*Primary Examiner*—David M. Naff
*Attorney, Agent, or Firm*—Holman & Stern

[57] ABSTRACT

Proteins and non-protein affinity ligands are covalently bonded to trichloro-s-triazine activated supports. The activated support is prepared by reacting a water-free insoluble solid support with trichloro-s-triazine in a non-aqueous medium and neutralizing HCl generated during the reaction with a tertiary amine which does not form an insoluble complex with the trichloro-s-triazine.

16 Claims, 2 Drawing Figures

- ● EACA, with CNBr
- ○ Albumin, with CNBr
- ■ EACA, with TsT
- □ Albumin, with TsT

PREPARATION OF TRICHLORO-S-TRIAZINE ACTIVATED SUPPORTS FOR COUPLING LIGANDS

The invention described herein was made in the course of work under a grant or award from the Department of Health, Education and Welfare.

BACKGROUND AND SUMMARY OF THE INVENTION

The present invention is concerned with new methods and reagents for coupling proteins and a wide variety of non-protein affinity ligands by strong covalent chemical bonds to solid-phase supports for the preparation of solid-phase catalysts and biospecific adsorbents.

Biospecific adsorbents have become very important tools for the isolation of biologic macromolecules, while immobilized enzymes have found wide use as durable, solid-phase catalysts. Such materials are prepared by chemically linking enzymes, inhibitors, or other biospecific compounds to a solid-phase support. Various methods and reagents have been described for the purpose of coupling, but each has its peculiar drawbacks, including: (a) weak chemical bonding; (b) ionic bonds; (c) necessity for strong conditions such as high temperature and pH to drive the reaction; (d) ride reactions; and (e) limited range of chemical groups with which the coupling reagent can react.

Previously coupling reagents include the reagent most widely utilized as a coupler, cyanogen bromide, as described by Jacoby et al. in *Methods Enzymol.* 34, 1974. This reagent is reacted with support such as agarose and cellulose in strongly alkaline solution where numerous side reactions occur. The cyanogen bromide-activated support subsequently reacts poorly with nucleophiles other than alkylamines, a severe limitation on the kinds of enzymes, ligands and other compounds which can be coupled. The coupling bonds, probably isourea bonds, are only moderately stable, and substantial amounts of the bound substance may "bleed" under practical conditions. This instability limits the useful life of the adsorbent or solid-phase catalyst and may add undesirable or potentially toxic contaminants to the product. Moreover, these isourea bonds are positively charged at neutral pH and can cause non-specific adsorption.

In contrast, reagents of a type that can provide strong covalent bonds between diverse supports and various nucleophilic groups of ligands under mild conditions have been employed in the dye industry since the introduction of "reactive" dyes. The most versatile and widely employed of these coupling reagents is trichloro-s-triazine (TsT). This reagent contains three reactive chlorines, the first of which is displaced to give a substituted dichloro-s-triazine (DsT), and the second to give a disubstituted monochloro-s-triazine (MsT). Conditions for controlled substitutions by various nucleophiles have received comparatively little study.

Like cyanogen bromide, TsT has been reacted with supports in strongly alkaline aqueous media where hydrolytic side reactions predominate. In the procedure as described by Kay et al. in *Nature* 217:641, (1968), the amount of TsT which reacts with support and that which hydrolyzes are competitive functions of temperature, pH and reagent concentration, and the extent of activation of the support cannot be predicted accurately. Moreover, the activated support is also subject to hydrolysis. Recently, Kay and Lilly have introduced the less reactive coupler, 2-amino-4,6-dichloro-s-triazine, as discussed in *Biochim. Biophys. Acta.* 198:276 (1970). However, in alkaline aqueous media, this reagent is subject to the same drawbacks as TsT during the activation reaction and, in addition, vigorous conditions are required for coupling the ligands. The major problems with such prior art methods are: (1) couplers are used empirically as others have used cyanogen bromide; (2) although triazine coupling provides strong bonds between support and proteins, no attention has been previously paid to competitive hydrolytic side reactions and to the introduction of adsorptive ionic sites; (3) the amount of ligand incorporated cannot be accurately controlled or predicted; and (4) the procedures are not satisfactory for the incorporation of small ligands in organic phase.

In order to circumvent the problem of TsT hydrolysis and to perform step-wise reactions at individual chlorines of TsT, by the present invention there have been developed methods for reaction in non-aqueous media. The critical conditions were found to include appropriate polar organic solvents and suitable organic bases to neutralize the HCl generated. With polyol supports like cellulose or cross-linked agarose, as described by Porath et al. in *J. Chromatogr.* 60:167 (1971), reactions with TsT have been found to occur smoothly and predictably in organic phase to give a (DsT)-dichloro-s-triazine substituted support. This activated support could be reacted in organic phase at one or both remaining chlorines, depending upon the nucleophiles involved and the reaction conditions.

It has also been found, in accordance with the present invention, that weak nucleophiles such as aniline react at room temperature in organic solvent with one of the chlorines of the DsT-support, leaving a single site for subsequent reaction. In fact, the initial "activation" reaction could be well controlled without side reactions to give a DsT-support; and a subsequent reaction with a weak nucleophile could be performed without side reactions to give an MsT-support. Finally, the single remaining chlorine of the MsT-support is less reactive than the DsT-support or TsT and is less susceptible to hydrolysis at moderate pH and temperature. Therefore, it can be reacted with nucleophiles in organic or in aqueous solution under mild conditions of pH and temperature to give the desired products.

In *J. Biol. Chem.* 252, 3578 (1977) Abuchowski et al. have reported the covalent attachment of polyethylene glycol (PEG) to proteins using TsT as a linking agent. While the coupling of an aliphatic alcohol to TsT in organic phase is the initial reaction in both the Abuchowski et al. procedure and in the present invention, this initial coupling is the entire extent of any similarity.

In their initial coupling reaction, Abuchowski et al. use benzene as a solvent for both PEG and TsT and use $Na_2CO_3$ to neutralize the HCl generated. This method, while adequate only for the coupling of TsT and PEG in solution phase, is not satisfactory for the coupling of TsT and any of the solid-phase supports utilized in affinity preparations, such as Sepharose, cellulose or polyvinyl alcohol. Benzene has proved to be a poor medium for reactions involving Sepharose and other hydrophilic polymers, most likely because of the non-polar nature of benzene. A major problem in the case of Sepharose or other polymers initially in aqueous phase is the transfer to benzene. It has also been observed that benzene seems to have an adverse effect on Sepharose structure. Furthermore, benzene is not a particularly good solvent for TsT, as discussed in a "s-Triazines and Derivatives," in *The Chemistry of Heterocyclic Compounds* (E. M. Smolin and O. Rapoport, eds.). Interscience Publishers, Inc., New York, Vol. 13, 1959.

Neutralization of the HCl generated is inefficient when the base is insoluble, as is the case of $Na_2CO_3$ in benzene. Inefficient neutralization of the HCl could permit conversion of the alcohol to the corresponding alkyl chloride, a side reaction known to occur under these conditions. Also, incorporation of chlorine into the Sepharose matrix is likely to impart undesirable properties.

By the present invention, there has been achieved the ability to circumvent many of the problems inherent in the Abuchowski et al. procedure, by conducting the initial activation reaction in dioxane or other organic solvents and by neutralizing the HCl generated with a soluble organic base such as N,N-diisopropylethylamine or other tertiary amine which does not form an insoluble complex with TsT in organic phase. Of the several reaction media which have been tried, dioxane was found to be best as it is both compatible with Sepharose and other hydrophilic polymers and is also a superior solvent for TsT. The use of a soluble organic base is also novel, and selection of the correct base is critical as most form insoluble complexes with TsT.

After the initial activation step, the two procedures are obviously different. Abuchowski et al. are satisifed with empirical coupling of dichloro-s-triazine-PEG to proteins in aqueous phase under alkaline conditions. The reference also states that a considerable excess of activated PEG must be used because hydrolysis of the second chlorine of the triazine occurs readily. This is a common feature of triazine reactions in aqueous or mixed aqueous-organic phase and it prevents accurate control and predictability of the reaction.

Unreacted and hydrolyzed PEG-dichloro-s-triazine are, of course, soluble and and separable from the PEG-coupled protein. This is not the case, however, if one wants a broader objective, i.e., coupling of an insoluble solid-phase compound such as cellulose-dichloro-s-triazine to a ligand where any side reactions such as hydrolysis affect the desired product. In the procedure of the present invention, control is established by replacing the second triazine chloride by a weak nucleophile such as aniline. This leaves a single chlorine available for reaction with nucleophilic groups of the proteins or other substances to be immobilized. This single chlorine can be replaced quantitatively by aliphatic amines under mold conditions, yet it does not hydrolyze readily below pH 9 at room temperature.

Various supports (polyols) can be reacted with TsT in accordance with the present invention, but all such supports must be rid of water prior to the initial reaction. Where suitable, drying can be performed by heating in vacuo, or water may be displaced from the support by washing with dry, miscible organic solvents such as 1,4-dioxane, acetonitrile and similar solvents. In addition, the parameters of the reaction conditions can be altered to effect changes in the amount of TsT which reacts with the support, including changes in reaction temperatures, reagent concentration, and the duration of the reaction.

The reaction of TsT with the support in organic phase requires the presence of a suitable organic base. The bases generally employed in analogous acyl chloride type reactions such as triethylamine, pyridine, N-ethyl morpholine, and lutidine, were found to form insoluble complexes with TsT in organic solvents. However, it was found that tertiary amines such as N,N-dimethylaniline and N,N-diisopropylethylamine did not form such complexes and performed satisfactorily.

BRIEF DESCRIPTION OF THE DRAWINGS

The advantages and features of the present invention will be more fully understood from the following description of the preferred embodiments, taken in conjunction with the accompanying drawings, wherein.

DESCRIPTION OF THE PREFERRED EMBODIMENTS

Figure 1:
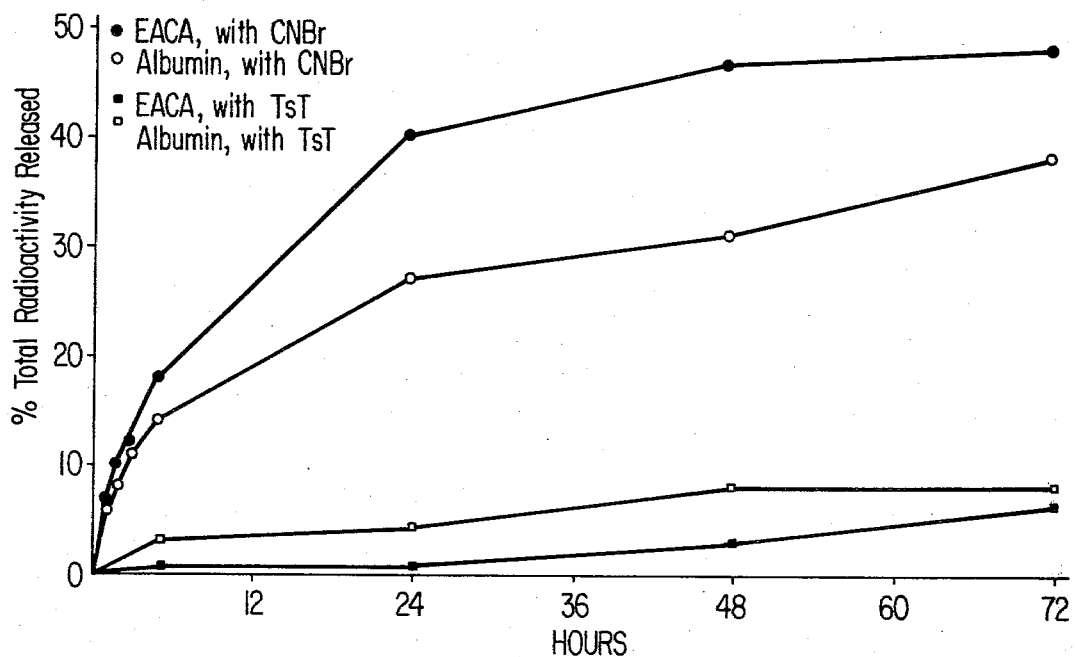
FIG. 1 is a graph showing a comparison of the stability of ligands attaches with CNBr to those attached with TsT.

The following is a general procedure for the preparation of the reactions of triazine-linked bioaffinity resins beginning with an aqueous suspension of support such as cross-linked agarose. This procedure is set forth schematically as follows:

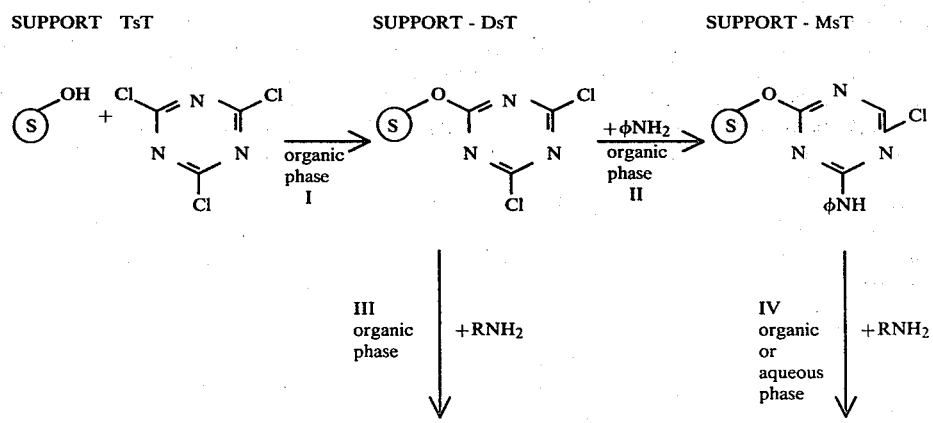

-continued

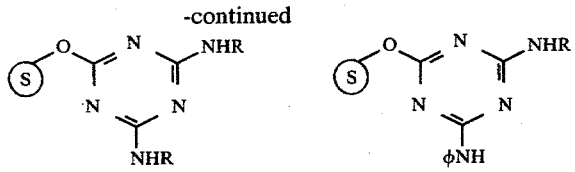

An aqueous suspension of the support is washed with a series of dioxane-water solutions in which the amount of dioxane increases from 0 to 100%. The support is transferred to a round bottom flask equipped with a glass-sealed stirrer and water condenser. Transfer is accomplished with a small amount of dioxane. The reaction flask is immersed in a thermostated oil bath and its contents stirred at low speed. N,N-diisopropylethylamine or N,N-dimethylaniline in dioxane is added and the reaction is allowed to equilibrate. The reaction is initiated by the addition of trichloro-s-triazine dissolved in dioxane. Generally, fluid and solid phases are of equal volume, and base concentration is twice that of the trichloro-s-triazine. The amount of triazine incorporated into the support resin depends on trichloro-s-triazine concentration, length of reaction and reaction temperature.

The activated DsT support is then washed with several bed volumes of dioxane. At this point the activated support can be reacted in several different ways: (1) it can be reacted in organic dioxane with a strong nucleophile such as an alkyl amine to give a dialkyl-triazine-resin; (2) it can be reacted in dioxane with a weak nucleophile such as an aryl amine to give a monoaryl-triazine-resin with a chlorine still available for further reaction; (3) the monoaryl-triazine-resin can be washed with dioxane-water solutions containing decreasing amounts of dioxane and the resin, now in aqueous solution, can be reacted with either proteins or other nucleophiles; or (4) the organic solvent can be removed from the monoarylmonochloro-s-triazine-resin by freeze-drying or other gentle means and the dried, activated resin stored for later use.

EXAMPLE 1

As a specific example, 100 ml of Sepharose CL-4B was washed with 200 ml of a mixture of water:dioxane (30:70) followed by 200 ml water:dioxane (70:30) and finally by 1000 ml dioxane. Washing was accomplished on a sintered glass funnel under vacuum. The resin was allowed to stand overnight in a glass stoppered graduated cylinder to accurately measure the bed volume and, after removing the excess dioxane, the settled gel was transferred with 60 ml dioxane to a 500 ml 3-necked round bottom flask equipped with a water jacketed condenser and a glass-sealed stirrer. The reaction flask was immersed in a thermostated oil bath maintained at 50°±2° C. and the contents were stirred at 100 rpm. The amount of 20 ml of 2 M N,N-diisopropylethylamine in dioxane was then added. After 30 min, 20 ml of 1 M trichloro-s-triazine in dioxane was added to initiate the reaction. After 60 min at 50°, the activated resin was washed on a sintered glass funnel with 1000 ml of dioxane. The resin was found to contain 112 μmoles triazine per gram of resin. A portion of the resin was then reacted with 2 volumes per bed volume of resin, of 1 M ethylene diamine in dioxane, for 30 min, at room temperature and was found to couple 244 μmoles of diamine per gram of resin.

A second portion was reacted with 2 volumes of aniline in dioxane at room temperature for 30 min. and was subsequently washed with 5 bed volumes of dioxane on a sintered glass funnel. A portion of this latter resin was reacted with 2 bed volumes of 1 M ethylenediamine in dioxane at room temperature for 30 min and was found to couple 112 μmoles of diamine per gram of resin. A second portion of the aniline-treated resin was washed with 2 bed volumes of water:dioxane (70:30) at 4° C. and finally by 10 bed volumes of water at 4° C. on a sintered glass funnel.

A portion of the resin in aqueous phase was incubated with 2 bed volumes of 0.66 M epsilon amino caproic acid, 0.30 M sodium borate, 0.30 M sodium chloride buffer, pH 8.5, for 22 hours at room temperature, after which time 116 μmoles of 6-aminohexanoic acid was incorporated into the resin. Another portion of the resin in aqueous phase was reacted with 4 bed volumes of a solution of bovine serum albumin, 10 mg/ml in 0.30 M sodium borate, 0.30 M sodium chloride buffer, pH 8.0, for 22 hours at room temperature. This resin was found to have coupled 42.3 mg of protein per gram of resin.

EXAMPLE 2

To compare the stability of ligands attached to agarose with CNBr to those attached with TsT, $^{14}$C-bovine serum albumin (BSA) and $^{14}$C-EACA were each coupled to Sepharose CL-6B using these two coupling reagents. The resins were then treated under conditions which would accelerate hydrolysis of the coupling bonds, namely elevated temperature and pH as shown in FIG. 1. The graph of FIG. 1 shows the results of hydrolysis of $^{14}$C-EACA-Sepharose and $^{14}$C-BSA-Sepharose in 0.33 M Na$_2$CO$_3$, pH 11.2 at 50° C. Packed resin was suspended in buffer and at the indicated intervals aliquots were removed and assayed for radioactivity. Total radioactivity represents the total amount of ligand bound to the resin. $^{14}$C-EACA and $^{14}$C-BSA alkylated with $^{14}$C-iodoacetamide and containing 0.6 mole carboxyamidomethyl groups per mole of protein (1.8×10$^5$ cpm/mg) prepared in accordance with procedures set forth, for example, by Finlay et al., *J. Biol. Chem.* 245, 5258 (1970), were coupled to CNBr-activated Sepharose CL-6B in 0.3 M Na Borate, 0.3 M NaCl, pH 8.0, by the procedure outlined by Parikh et al. in *Methods Enzymol.* 34:77 (1974). The BSA-Sepharose linked with CNBr contained 35.3 mg of protein/g resin and the EACA-Sepharose contained 317 μmoles of amine/g resin. $^{14}$C-BSA and $^{14}$C-EACA were coupled to triazine-activated Sepharose CL-6B in 0.22 M Na borate, 0.22 M NaCl, pH 8.0. The BSA-Sepharose prepared by triazine activation contained 42.3 mg of protein/g resin and the EACA-Sepharose contained 140 μmoles of amine/g resin. Packed resin, 1 ml, was suspended in 2.0 ml 0.5 M Na$_2$CO$_3$, pH 11.2, at 50°. At the intervals indicated in FIG. 1, the resin suspension was centrifuged and an aliquot from the supernatant fraction removed and counted. The data clearly show the triazine linkage to be superior to the CNBr linkage for both proteins and small molecule ligands.

Figure 2:
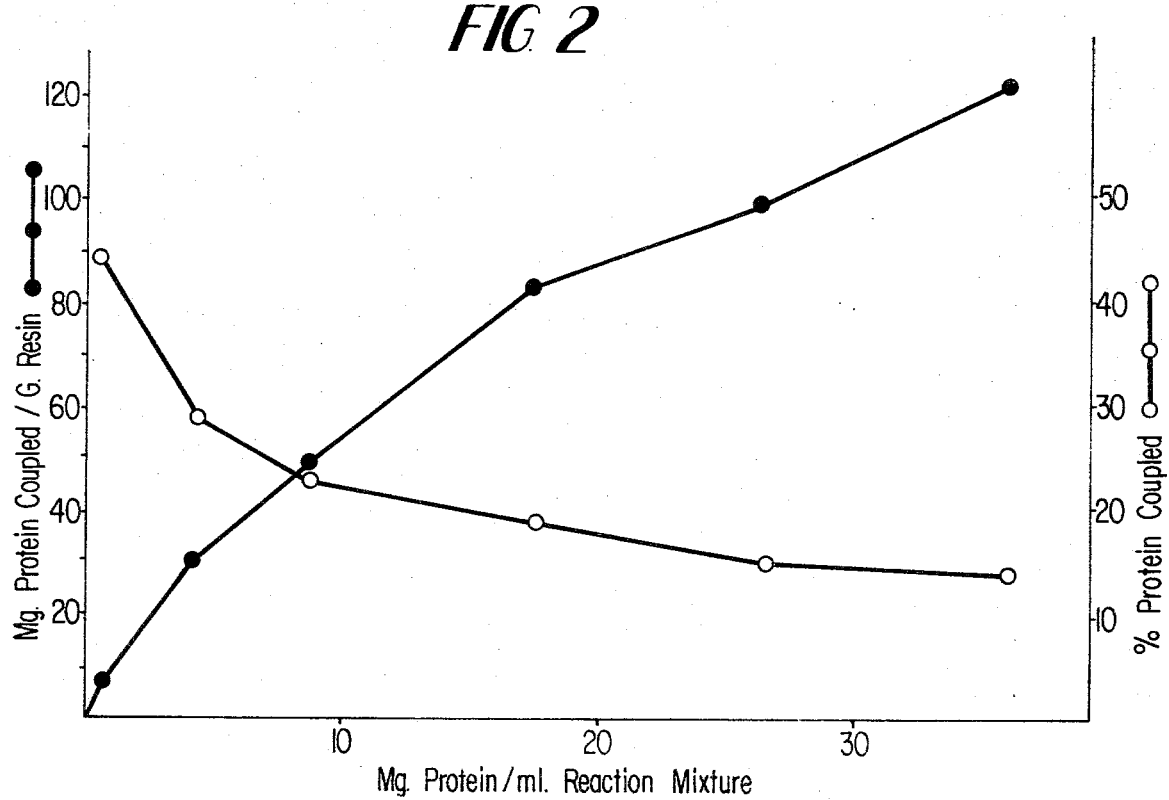
FIG. 2 is a graph showing various characteristics of protein coupled to TsT-activated resin.

Referring to FIG. 2, this graph shows that the amount of protein coupled to triazine activated resin is dependent on the amount of free protein present in the coupling reaction.

The data of FIG. 2 is concerned with the effect of coupling of bovine serum albumin to Sepharose CL-MsT. Samples of Sepharose CL-6BMsT (100 mg), lyophilized from dioxane, were suspended in 5.0 ml of 0.15 M NaCl, 0.1 M NaBorate, pH 8.0. After mixing at 0° for 1 min, the suspensions were centrifuged and the supernatants aspirated to yield a total volume of resin plus liquid of 1.5 ml. $^{14}$C-CM-Bovine serum albumin in 1.0 ml of this same buffer was then added and the reactions were incubated with rocking at room temperature. After 44 hrs, the resins were washed with 1.0 M Tris-HCl, pH 8.8, water and 50% ethanol and then lyophilized. The amount of protein coupled was calculated after counting of weighed aliquots of the dried resin. It is interesting to note that with this particular lot of resin, 125 mg of albumin was coupled per gram with no indication that the resin had become saturated.

In Table I it is shown that in the pH range of 6-9, temperature has a greater effect on coupling efficiency than does pH. In preparing the information as shown in Table I, samples of Sepharose CL-MsT (100 mg) lyophilized from dioxane, were suspended in 5.0 ml buffer (pH 6 and 7:0.1 M NaPhosphate; pH 8 and 9:0.1 M NaBorate) containing 0.15 M NaCl. After mixing at 0° C. for 1 min, the suspensions were centrifuged and the supernatants aspirated to yield a total volume of resin plus liquid of 1.9 ml. $^{14}$C-CM bovine serum albumin (0.1 ml, 9.98 mg, 1.17×10$^5$ cpm) was added and the reactions were incubated with rocking for 24 hrs. Samples were washed and counted as described in connection with FIG. 1.

TABLE I

Coupling of Bovine Serum Albumin to Sepharose CL -MsT; Effect of temperature and pH

| Temperature | pH | mg protein coupled g resin |
|---|---|---|
|  | 6 | 19.7 |
|  | 7 | 19.8 |
| 8° |  |  |
|  | 8 | 20.7 |
|  | 9 | 21.5 |
|  | 6 | 28.0 |
|  | 7 | 26.2 |
| 27° |  |  |
|  | 8 | 30.2 |
|  | 9 | 33.3 |
|  | 6 | 36.1 |
|  | 7 | 45.9 |
| 45° |  |  |
|  | 8 | 51.1 |
|  | 9 | 48.9 |

In Tables II and III there are listed some of the enzymes, other proteins and other substances which have been coupled to TsT-activated Sepharose. Of the enzymes which have been coupled in accordance with the present invention, the one with the greatest commercial value is probably bacterial α-amylase which converts starch to dextrins and is used in the paper and textile industries and in the production of glucose.

In preparing the information as shown in Table II, reaction mixtures contained 100 mg of activated resin in a total volume of 2.0 ml 0.1 Na Borate, 0.15 M NaCl, pH 8.0 at the protein concentration indicated the first column of Table II. Reactions were conducted at 25°±2° C. with gentle rocking for 24 hours. The resins were then washed by filtration first with 1.0 M tris-Cl, pH 8.8 followed by 0.05 M tris-Cl, 0.15 M NaCl, pH 8.3. Resins were assayed for protein and enzymic activity as described previously.

It is thought that the invention and many of its attendant advantages will be understood from the foregoing description, and it will be apparent that various changes may be made in the methods as described herein without departing from the spirit and scope of the invention or sacrificing its material advantages, the forms hereinbefore described being merely preferred embodiments thereof.

TABLE II

COUPLING OF ENZYMES TO Sepharose CL-6B WITH TsT IN AQUEOUS PHASE AT pH 8

| ENZYME | COUPLING CONCENTRATION (MG/ML) | % PROTEIN BOUND | ENZYME COUPLED AS PROTEIN | MG/G RESIN AS ACTIVITY | % ACTIVITY |
|---|---|---|---|---|---|
| δ-Amylase | 3.9 | 13.2 | 10.2 | 6.2 | 60.2 |
| Lactic Dehydrogenase | 3.7 | 48.9 | 36.2 | 3.3 | 9.1 |
| Cellulase | 4.5 | 8.3 | 7.5 | 1.2 | 16.0 |
| Trypsin | 4.3 | 35.9 | 30.9 | 3.6A | 11.7 |
| Chymotrypsin | 4.3 | 36.2 | 31.1 | 2.9 | 9.3 |

TABLE III

LIGANDS ATTACHED TO CL-SEPHAROSE WITH TsT IN AQUEOUS PHASE

| Ligand | Amount Coupled/g Resin | Biological Acitivity |
|---|---|---|
| Fibrinogen | 28–142 mg | As fibrin-Sepharose, adsorbs 24–130 mg fibrinogen per G resin |
| Antifibrinogen | 15 mg | Adsorbs fibrinogen |
| Albumin | 28–125 mg | Adsorbs antialbumin |
| Histone | 48 mg | Substrate for proteolytic enzymes (as 125I histone-Sepharose) |
| Trypsin | 30–36 mg | 10% activity of unbound enzyme |
| Chymotrypsin | 45–75 mg | 10–25% activity of unbound enzyme |
| Lysine | 115 μmoles | Adsorbs 675 CTA units plasminogen per g resin |
| 6-Amino Caproic Acid | 120 μmoles |  |
| Benzamidine | 150 μmoles | Adsorbs 15 mg trypsin, 7 mg thrombin per g resin |
| Heparin | 3–6 mg | Adsorbs 3–6 mg antithrombin-III per g resin |

The embodiments of the invention in which an exclusive property or privilege is claimed are defined as follows:

1. In a method for coupling substances selected from the group consisting of protein ligands and non-protein affinity ligands by covalent chemical bonds to insoluble solid supports for the preparation of solid phase catalysts and biospecific adsorbents comprising the steps of reacting the insoluble solid support material with trichloro-s-triazine to produce an activated support and thereafter, coupling the ligand to the activated support, the improvement wherein the production of the activated support is carried out by the steps comprising:
   (a) reacting a water-free insoluble solid support material with trichloro-s-triazine in a non-aqueous medium comprising an organic solvent which is compatible with the support material and is also a solvent for trichloro-s-triazine;
   (b) neutralizing the HCl generated during the reaction with a tertiary amine which is soluble in said organic solvent and which does not form an insoluble complex with trichloro-s-triazine in said organic solvent; and
   (c) washing the obtained dichloro-s-triazine activated support with an additional amount of said organic solvent.

2. The method of claim 1 wherein the tertiary amine is selected from the group consisting of N,N-diisopropylethylamine and N,N-dimethylaniline.

3. The method of claim 1 wherein, in step (d) said organic solvent is selected from the group consisting of dioxane and acetonitrile.

4. The method of claim 1 including the further step of adding a nucleophile to the washed trichloro-s-triazine activated support in an organic solvent to replace one or both of chlorine atoms on the triazine ring, and when both chlorine atoms are replaced, the nucleophile is said ligand.

5. The method of claim 4 wherein said nucleophile is selected from the group consisting of aliphatic amines, aryl amines, phenols and alkoxyl amines.

6. The method of claim 1 including the further step of adding a weak nucleophile to the washed dichloro-s-triazine activated support in an organic solvent to replace a single chlorine atom on the triazine ring, leaving the remaining chlorine atom available for further replacement by said ligand.

7. The method of claim 6 wherein said weak nucleophile is aniline.

8. The method of claim 6 wherein the monochloro-s-triazine activated support is dried for storage and later coupling with said ligand.

9. The method of claim 1, wherein said support material initially contains water and is pretreated prior to step (a) to remove said water therefrom.

10. The method of claim 9 wherein said pretreatment of said support material is accomplished by washing the support material with an organic solvent.

11. The method of claim 9 wherein said pretreatment of said support material is accomplished by drying the support material under vacuum.

12. The method of claim 1 wherein said protein ligand is an enzyme.

13. A support coupled ligand obtained in accordance with the method of claim 1, wherein said non-aqueous medium consists essentially of dioxane or acetonitrile.

14. A support-coupled ligand obtained in accordance with the method of claim 8, wherein said non-aqueous medium consists essentially of dioxane or acetonitrile.

15. A support-coupled ligand produced by the method of claim 4, wherein said non-aqueous medium consists essentially of dioxane or acetonitrile.

16. A support-coupled ligand produced by the method of claim 6, wherein said non-aqueous medium consists essentially of dioxane or acetonitrile.

* * * * *

UNITED STATES PATENT AND TRADEMARK OFFICE
CERTIFICATE OF CORRECTION

PATENT NO. : 4,229,537
DATED : October 21, 1980
INVENTOR(S) : LEONARD T. HODGINS, et al It is certified that error appears in the above-identified patent and that said Letters Patent are hereby corrected as shown below:

Claim 3, line 1, delete ", in step (d)".

Signed and Sealed this

Seventeenth Day of February 1981

[SEAL]

Attest:

RENE D. TEGTMEYER

Attesting Officer  Acting Commissioner of Patents and Trademarks